US012697101B2

(12) United States Patent
Nikolov et al.

(10) Patent No.: US 12,697,101 B2
(45) Date of Patent: Aug. 4, 2026

(54) ADAPTIVE ULTRASOUND IMAGING ACQUISITION

(71) Applicant: GE Precision Healthcare LLC, Waukesha, WI (US)

(72) Inventors: Svetoslav Ivanov Nikolov, Søborg (DK); Per Haugaard, Skovlunde (DK); Fredrik Gran, Limhamn (SE); Mikkel Schou, Roskilde (DK)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 0 days.

(21) Appl. No.: 18/829,982

(22) Filed: Sep. 10, 2024

(65) Prior Publication Data

US 2026/0069254 A1 Mar. 12, 2026

(51) Int. Cl.
*A61B 8/00* (2006.01)

(52) U.S. Cl.
CPC .............. *A61B 8/54* (2013.01); *A61B 8/4483* (2013.01); *A61B 8/461* (2013.01); *A61B 8/5269* (2013.01); *A61B 8/467* (2013.01)

(58) Field of Classification Search
CPC ......... A61B 8/54; A61B 8/4483; A61B 8/461; A61B 8/5269; A61B 8/467
See application file for complete search history.

*Primary Examiner* — Pascal M Bui Pho
*Assistant Examiner* — Nicholas A Robinson
(74) *Attorney, Agent, or Firm* — Daugherty & Del Zoppo, Co. LPA

(57) ABSTRACT

An ultrasound imaging system includes a transducer array configured to transmit in a first transmission mode or a split transmission mode in which an original transmission of the first transmission mode is split into multiple transmissions for each scanline. The system further includes a beamformer configured to beamform an echo signal corresponding to the original transmission or a combination of echo signals corresponding to the multiple transmissions. The system further includes a scanline processor configured to adaptively apply digital time gain compensation to each scanline, wherein a first gain is applied to a scanline corresponding to a transmission traversing tissue and a second gain is applied to a scanline corresponding to a transmission traversing a water standoff. The system further includes a controller configured to switch from the first transmission mode to the split transmission mode in response to detecting water standoff enhancement artifact.

20 Claims, 9 Drawing Sheets

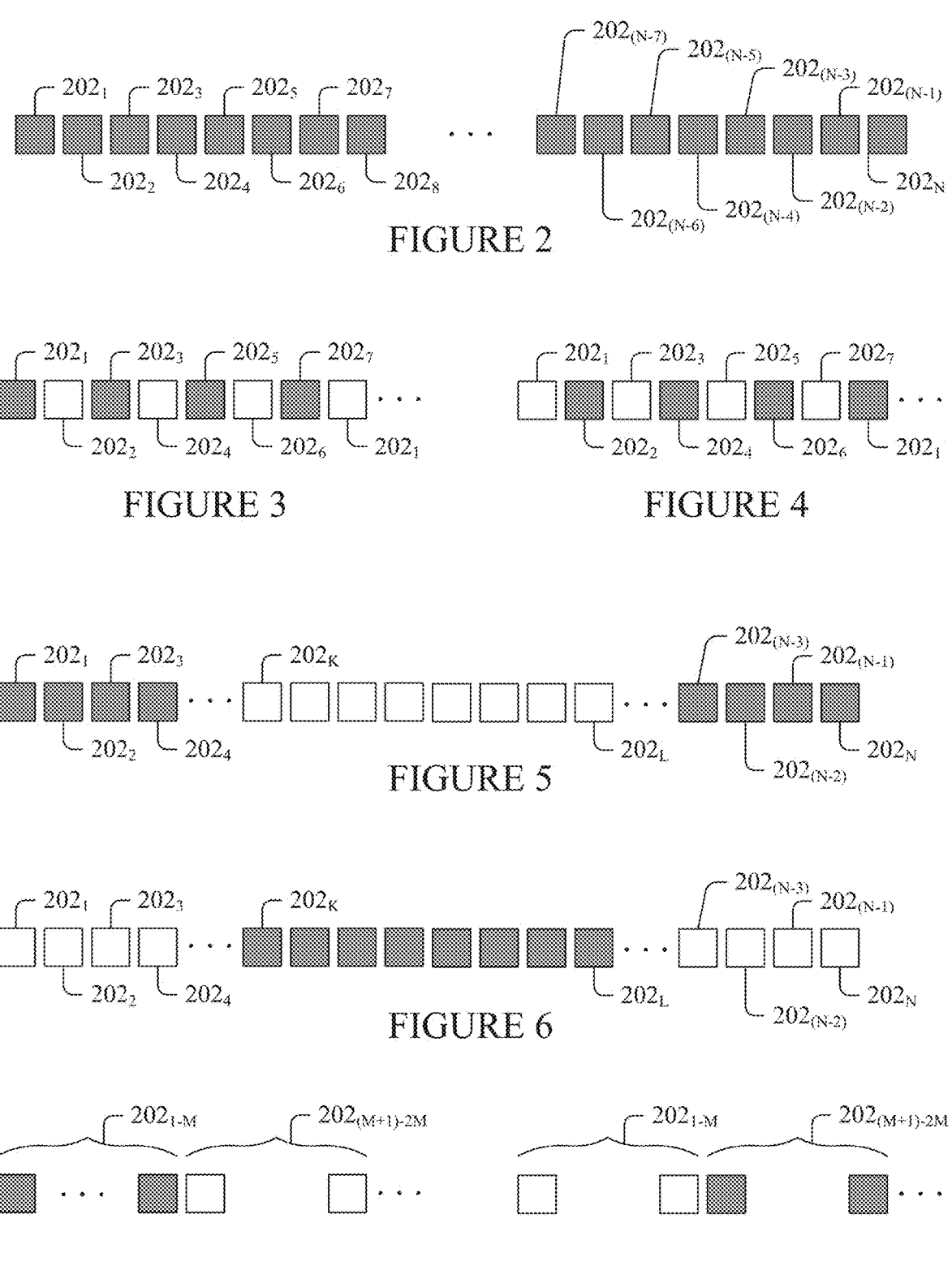

Figures 9, 10:
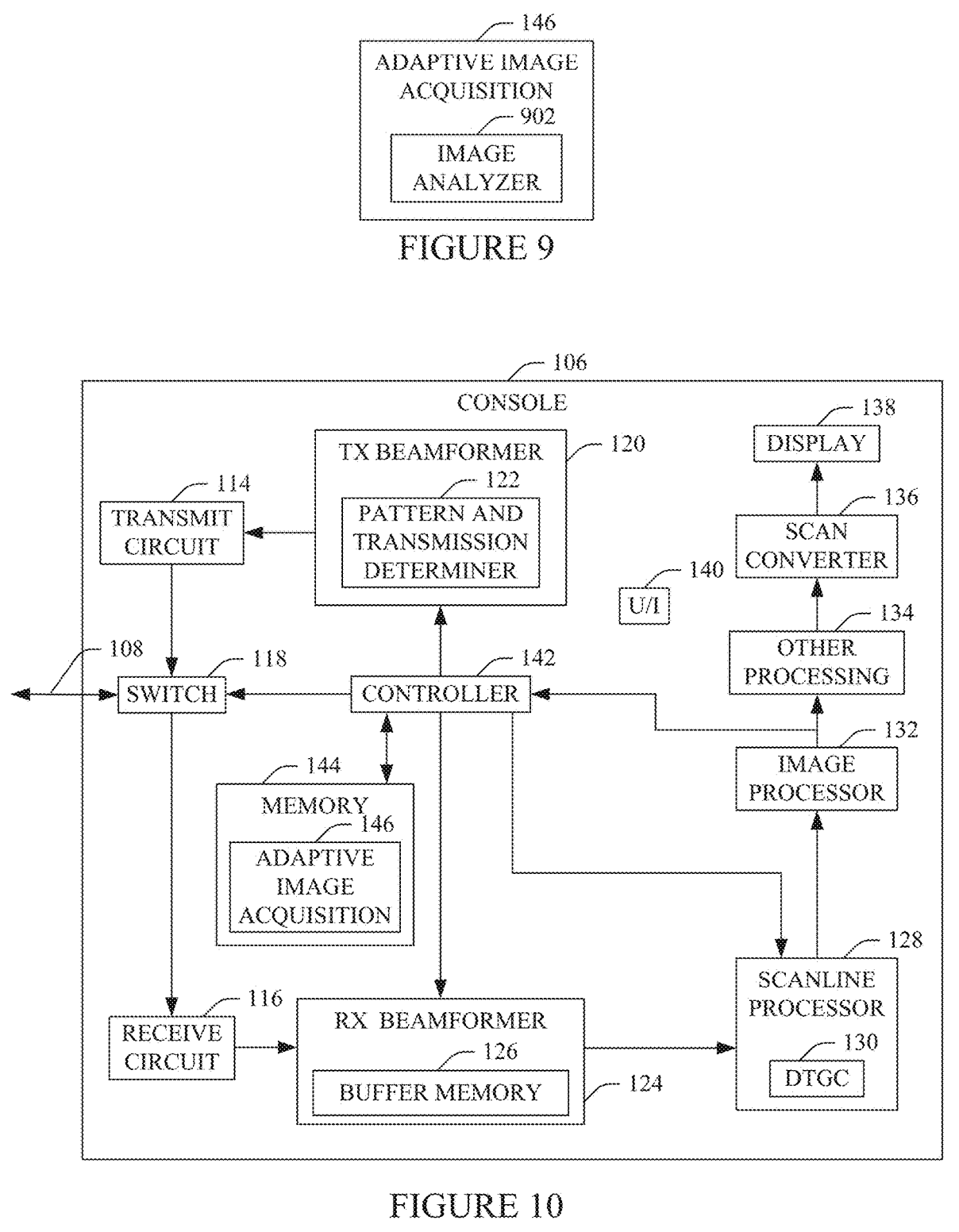

146

ADAPTIVE IMAGE
ACQUISITION

902

IMAGE
ANALYZER

CONSOLE

TX BEAMFORMER — 120

122

PATTERN AND
TRANSMISSION
DETERMINER

DISPLAY — 138

114

TRANSMIT
CIRCUIT

SCAN
CONVERTER — 136

U/I — 140

108

SWITCH — 118

CONTROLLER — 142

OTHER
PROCESSING — 134

IMAGE
PROCESSOR — 132

144

MEMORY
146

ADAPTIVE
IMAGE
ACQUISITION

SCANLINE
PROCESSOR — 128

116

RECEIVE
CIRCUIT

RX BEAMFORMER

126

BUFFER MEMORY — 124

130

DTGC

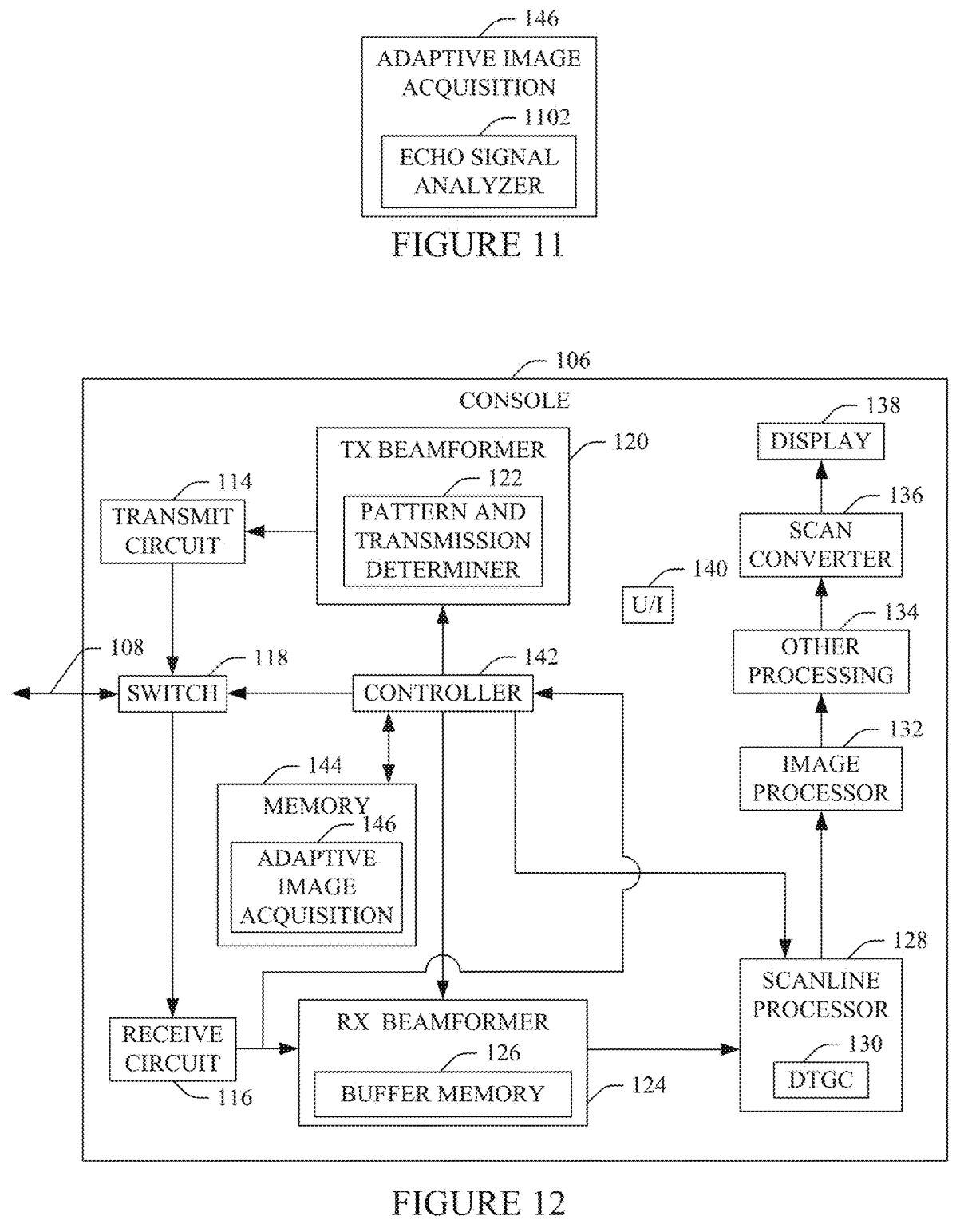

ADAPTIVE IMAGE
ACQUISITION
1102

ECHO SIGNAL
ANALYZER

CONSOLE

138

DISPLAY

TX BEAMFORMER
120

122

PATTERN AND
TRANSMISSION
DETERMINER

136

SCAN
CONVERTER

114

TRANSMIT
CIRCUIT

140

U/I

108

SWITCH
118

CONTROLLER
142

134

OTHER
PROCESSING

144

MEMORY
146

ADAPTIVE
IMAGE
ACQUISITION

132

IMAGE
PROCESSOR

128

SCANLINE
PROCESSOR

130

DTGC

RECEIVE
CIRCUIT
116

RX  BEAMFORMER
126

BUFFER MEMORY
124

FIGURE 12

ADAPTIVE ULTRASOUND IMAGING ACQUISITION

FIELD

The following generally relates to ultrasound imaging, and, more particularly to adaptive ultrasound imaging acquisition, and finds particular application to adaptive ultrasound imaging acquisition to mitigate water standoff enhancement artifact.

BACKGROUND

Ultrasound imaging provides a real-time image with information about the interior of an object or a subject such as tissue, organs, etc. With one example, an excitation pulse is provided to a transducer array. At least a sub-set of the elements of the array receive the pulse and converts the electrical pulse to a pressure wave/ultrasound signal. The pressure wave is transmitted by the transducer array during a transmit operation, propagates in a medium, and interacts with the medium. Such interaction results in, among other things, echoes, which are reflections back towards the transducer.

The elements receive the echoes during a receive operation and convert the reflections to analog signals. For each receive operation, the analog signals are amplified, converted to digital signals, and beamformed to produce a scan line of radio frequency (RF) data. With delay-and-sum beamforming, the digital signals are time delayed, weighted, and then summed to produce the scan lines. The scan lines are further processed (e.g., band-pass filtering, envelope detection, logarithmic compression, etc.), scan converted, and displayed as frame/2-D image (e.g., a B-mode image).

An acoustic coupling material has been used between the ultrasound probe and the patient under examination. Such materials reduce or eliminate air pockets between the probe and the tissue, maintaining the strength of the ultrasound signal and mitigating image artifact, as ultrasound pressure waves travel poorly through air. With some procedures, ultrasound imaging is utilized not only before the procedure to confirm location and size of operated tumors, but also during and after procedure to check for residual tissue of interest that was excised during the procedure. With such a procedure, the acoustic coupling materials has included a water standoff.

For example, a particular procedure may involve excision of a tumor or other tissue of interest. An example of such a procedure is a neurosurgical procedure to remove a brain tumor from brain tissue. With such a procedure, ultrasound imaging has been employed after the excision to determine whether any residual tumor remains. The excision creates a cavity in tissue, and a water standoff has been used to fill the cavity and create an acoustic coupling. Without the water standoff, the cavity introduces an air pocket between the probe and the tissue. The tumor is either totally removed or remnants of the tumor remain close to the interface between the water standoff and the tissue.

Ultrasound pressure waves have a decreased echogenicity within a tumor. As such, pixels corresponding to tumor are darker than pixels of surrounding tissue. However, water has little attenuation to ultrasound pressure waves relative to tissue. As a consequence, the echoes at the water standoff-tissue boundary are large reflections and have enhanced intensity relative to echoes from ultrasound pressure waves that traverse only tissue. The large echoes result in bright pixels (enhancement artifact) at the water standoff-tissue boundary, which masks (or "hides") some or all of the residual tumor at the water standoff-tissue boundary. FIG. 17 shows an example of a water standoff in connection with excised tissue.

In FIG. 17, an ultrasound probe 1702 includes a transducing surface 1704. The transducing surface 1704 is above tissue 1706 and a cavity 1708 created from an excision. In FIG. 17, the cavity 1708 is filled with water 1710. Water standoff artifact manifests at a water standoff-tissue boundary 1712. In FIG. 17, ultrasound pressure waves emitted at an end region 1714 of the transducing surface 1704 traverse only the tissue 1706, whereas pressure waves emitted at a center region 1716 of the transducing surface 1704 traverse only the water 1710. In FIG. 17, ultrasound pressure waves in other regions partially traverse the water 1710 and partially traverse the tissue 1706.

Unfortunately, the digital time gain compensation (DTGC) applied to the scanlines cannot simply be lowered to reveal the hidden residual tumor at the water standoff-tissue boundary. For example, the large reflections may result in echo signals that have an intensity that is higher than a maximum capacity of the amplifiers of the analog front end, resulting in saturation. In this instance, portions of the signals are clipped and cannot be recovered by reducing the DTGC. In addition, lowering the DTGC applied to the scanlines traversing only tissue would degrade the image quality of those regions of the image.

In view of at least the foregoing, there is an unresolved need for an approach that mitigates pixel intensity enhancement artifact at a water standoff-tissue interface in ultrasound imaging.

SUMMARY

Aspects of the application address the above matters, and others. This summary introduces concepts that are described in more detail in the detailed description. It should not be used to identify essential features of the claimed subject matter, nor to limit the scope of the claimed subject matter.

In one aspect, an ultrasound imaging system includes a transducer array configured to transmit in either a first transmission mode or a split transmission mode in which an original transmission for a scanline of the first transmission mode is split into multiple transmissions for the scanline. The ultrasound imaging system further includes a beamformer configured to beamform either an echo signal corresponding to the original transmission or a combination of echo signals corresponding to the multiple transmissions. The ultrasound imaging system further includes a scanline processor configured to adaptively apply digital time gain compensation individually to each scanline, wherein a first gain is applied to a scanline corresponding to a transmission traversing tissue and a second gain is applied to a scanline corresponding to a transmission traversing a water standoff to correct for water standoff enhancement artifact. The ultrasound imaging system further includes a controller configured to switch the transducer array, the beamformer and the scanline processor from the first transmission mode to the split transmission mode in response to detecting water standoff enhancement artifact. The ultrasound imaging system further includes an image processor configured to generate an image based on a set of scanlines. The ultrasound imaging system further includes a display configured to display the image.

In one instance, each of the multiple transmissions has a transmit energy less than a transmit energy of the original transmission for the scanline. In another instance, an aggregate of the transmit energy of each of the multiple transmissions equals the transmit energy of the original transmission for the scanline. In another instance, the controller is configured to detect the water standoff enhancement artifact based on an analysis of the image. In another instance, the analysis of the image includes edge detection to detect a boundary of the water standoff in the image. In another instance, the controller is configured to detect the water standoff enhancement artifact based on an analysis of the echo signal. In another instance, the analysis of the echo signal identifies signal saturation. In another instance, the controller is configured to switch from the first transmission mode to the split transmission mode based on a user input. In another instance, the original transmission includes excitation of a predetermined set of elements of the transducer array, and the split transmission includes excitation of a first sub-set of the set of elements for a first transmission and excitation of a second sub-set of the set of elements for a second transmission of the transducer array. In another instance, the first sub-set and the second sub-set include a same number of elements from the set of elements.

In another aspect, a computer-implemented method includes transmitting in either a first transmission mode or a split transmission mode in which an original transmission for a scanline of the first transmission mode is split into multiple transmissions for the scanline. The computer-implemented method further includes beamforming either an echo signal corresponding to the original transmission or a combination of echo signals corresponding to the multiple transmissions. The computer-implemented method further includes adaptively applying digital time gain compensation individually to each scanline, wherein a first gain is applied to a scanline corresponding to a transmission traversing tissue and a second gain is applied to a scanline corresponding to a transmission traversing a water standoff to correct for water standoff enhancement artifact. The computer-implemented method further includes switching the transducer array, the beamformer and the scanline processor from the first transmission mode to the split transmission mode in response to detecting water standoff enhancement artifact. The computer-implemented method further includes generating an image based on a set of scanlines. The computer-implemented method further includes displaying the image.

In another aspect, a computer readable medium is encoded with computer executable instructions, which, when executed by a processor, cause the processor to transmit in either a first transmission mode or a split transmission mode in which an original transmission for a scanline of the first transmission mode is split into multiple transmissions for the scanline, beamform either an echo signal corresponding to the original transmission or a combination of echo signals corresponding to the multiple transmissions, adaptively apply digital time gain compensation individually to each scanline, wherein a first gain is applied to a scanline corresponding to a transmission traversing tissue and a second gain is applied to a scanline corresponding to a transmission traversing a water standoff to correct for water standoff enhancement artifact, switch the transducer array, the beamformer and the scanline processor from the first transmission mode to the split transmission mode in response to detecting water standoff enhancement artifact, generate an image based on a set of scanlines, and display the image.

Those skilled in the art will recognize still other aspects of the present application upon reading and understanding the attached description.

BRIEF DESCRIPTION OF THE DRAWINGS

The application is illustrated by way of example and not limited by the figures of the accompanying drawings in which like references indicate similar elements.

FIG. 2 schematically illustrates an example of a prior art single transmission per scanline acquisition.

FIG. 3 schematically illustrates an example of a first transmission of a split transmission that excites only odd numbered transducer elements, in accordance with an aspect of an embodiment(s) herein.

FIG. 4 schematically illustrates an example of a second transmission of the split transmission of FIG. 3 that excites only even numbered transducer elements, in accordance with an aspect of an embodiment(s) herein.

FIG. 5 schematically illustrates another example of a first transmission of a split transmission that excites only outer transducer elements, in accordance with an aspect of an embodiment(s) herein.

FIG. 6 schematically illustrates an example of a second transmission of the split transmission of FIG. 5 that excites only inner transducer elements, in accordance with an aspect of an embodiment(s) herein.

FIG. 7 schematically illustrates yet another example of a first transmission of a split transmission that excites only a first set of transducer elements, in accordance with an aspect of an embodiment(s) herein.

FIG. 8 schematically illustrates an example of a second transmission of the split transmission of FIG. 7 that excites only the remaining set of transducer elements, in accordance with an aspect of an embodiment(s) herein.

FIG. 9 schematically illustrates a non-limiting example of an adaptive image acquisition algorithm of the imaging system that includes an image analyzer, in accordance with an aspect of an embodiment(s) herein.

FIG. 10 schematically illustrates the ultrasound imaging configured with the example adaptive image acquisition algorithm of FIG. 9 with the image analyzer, in accordance with an aspect of an embodiment(s) herein.

FIG. 11 schematically illustrates a non-limiting example of an adaptive image acquisition algorithm of the imaging system that includes an echo signal analyzer, in accordance with an aspect of an embodiment(s) herein.

FIG. 12 schematically illustrates the ultrasound imaging configured with the example adaptive image acquisition algorithm of FIG. 11 with the echo signal analyzer, in accordance with an aspect of an embodiment(s) herein.

DETAILED DESCRIPTION

Embodiments of the present disclosure will now be described, by way of example, with reference to the figures, in which a system, a method and/or instructions on a computer readable medium mitigate water standoff enhancement artifact at a water standoff-tissue interface in ultrasound imaging. In one instance, this is achieved through identifying a presence of water standoff enhancement artifact at a water standoff-tissue boundary, automatically adjusting ultrasound pressure wave transmissions and receive beamforming, and adaptively adjusting scanline digital time gain compensation (DTGC) to mitigate water standoff enhancement artifact.

As discussed above, water standoffs have been used with procedures that include excising certain tissue of interest (e.g., a tumor, etc.) to fill the cavity created from the excision with water to avoid air pockets between the probe and the normal tissue, which can lead to decreased signal strength, image artifact, etc. However, water has little attenuation to ultrasound pressure waves relative to the tissue, and, as a consequence, the echoes at the water standoff-tissue interface in the cavity have enhanced intensity relative to echoes from ultrasound pressure waves that do traverse the water standoff, resulting in bright pixels at the water standoff-tissue boundary, masking some or all of any residual tissue of interest.

As described in greater detail below, in one instance the identification of a presence of water standoff enhancement artifact is based on image analysis of a B-mode image, signal analysis of the echo signals, a user input, etc. In any instance, in response to the identification of a presence of water standoff enhancement artifact, an energy of each transmission is reduced by splitting the transmission into multiple transmissions, each with a lower energy than the original transmission, and DTGC is applied individually to the scanlines based on the material each one traversed (e.g., only tissue, only water, both tissue and water). Splitting the transmission mitigates saturation, and applying the DTGC individually allows for compensating the scanlines traversing the water standoff.

Figure 1:
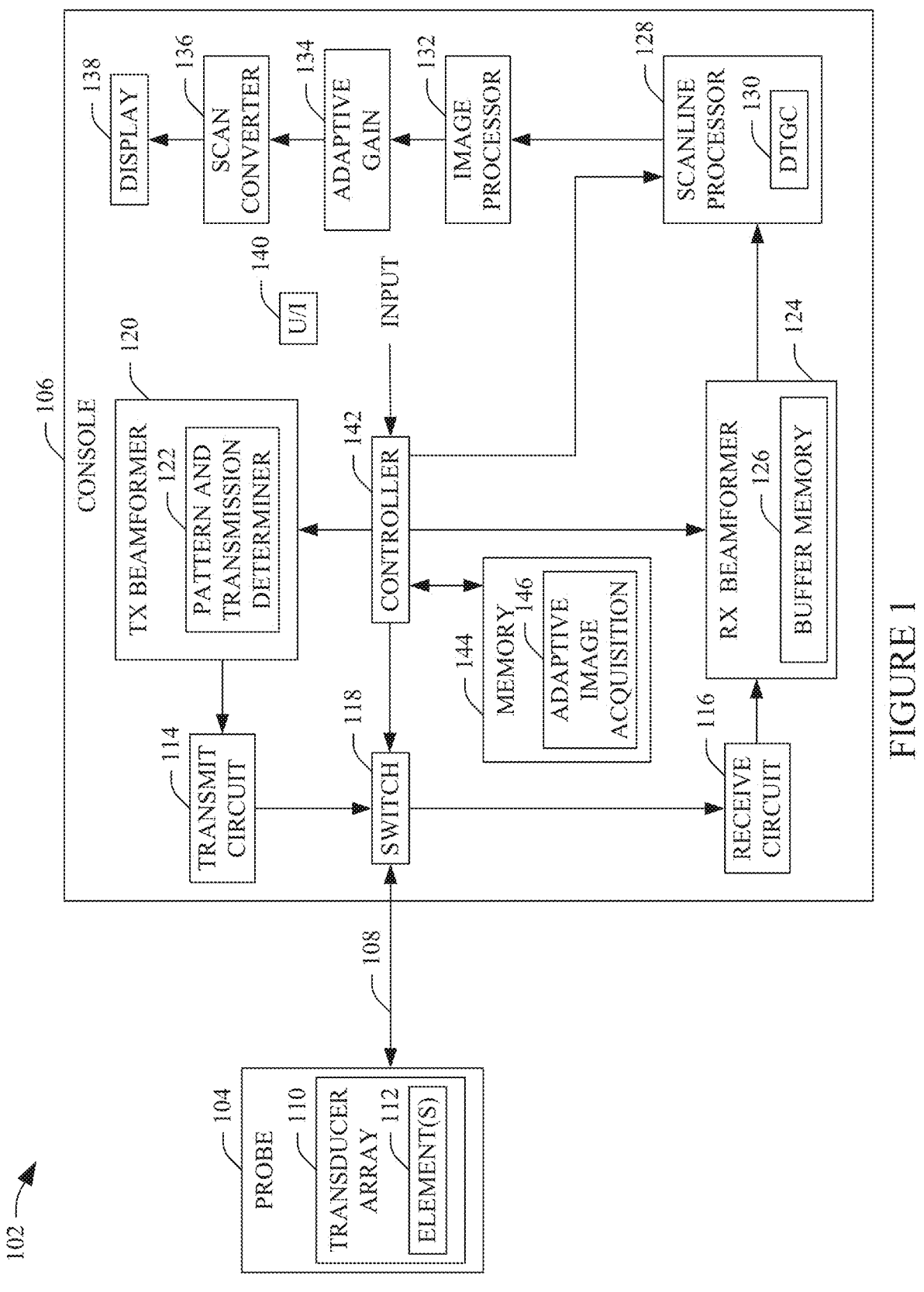
FIG. 1 schematically illustrates a non-limiting example of an ultrasound imaging system configured with adaptive imaging acquisition to mitigate water standoff enhancement artifact, in accordance with an aspect of an embodiment(s) herein.

Initially referring to FIG. 1, a non-limiting example of an ultrasound system 102 is schematically illustrated. The ultrasound system 102 includes an ultrasound probe 104 and a console 106. In the illustrated embodiment, the probe 104 and the console 106 interface with each other via a communication channel 108, which includes wired (e.g., complimentary interfaces and a cable therebetween) and/or wireless technology (e.g., Wi-Fi, etc.). In another instance, the probe 104 and the console 106 are integrated in a same housing such as part of a hand-held ultrasound system, etc.

The probe 104 includes a transducer array 110. The transducer array 110 includes one or more transducer elements 112. Examples of suitable arrays include 64, 128, 192, 256, and/or other arrays, including larger and smaller arrays, one dimensional (1-D) or two dimensional (2-D), etc. The transducer array 110 can be linear, curved, and/or otherwise shaped, fully populated, sparse and/or a combination thereof, etc. The one or more transducer elements 112 are configured to convert an excitation electrical signal to an ultrasound pressure field and convert a reflected ultrasound pressure field to an electrical signal.

By way of non-limiting example, the one or more transducer elements 112 can be selectively excited via an excitation electrical (pulsed) signal, which causes at least a sub-set of the transducer elements 112 to transmit an ultrasound pressure field into an examination or scan field of view. The ultrasound pressure field may include a focused ultrasound beam, a defocused (spherical) wave, and/or other ultrasound signal. The one or more transducer elements 112 receive echo signals and generate analog electrical signals indicative thereof. The echo signals are generated in response to the transmitted ultrasound pressure field interacting with structure, such as tissue, blood cells flowing in a portion of a vessel, etc.

The console 106 includes a transmit circuit 114 configured to generate the excitation electrical signal provided to transducer array 110 for transmitting the ultrasound pressure field. In one instance, this includes generating delays for individual elements 112 of the transducer array 110, e.g., for transmit focusing, beam steering, etc., exciting a full set of elements or, for a split transmission mode, less than the full set for each split transmission, where the combination of the split transmission excite the full set of elements.

The console 106 further includes receive circuit 116 configured to receive and pre-process the analog echo signals. In one instance, this includes one or more of applying a fixed amplification, applying analog time gain compensation (ATGC), converting the analog signals to digital signals (i.e. digitizing the signals), down converting to shift a center frequency of the signals to baseband, decimating the signal to reduce the data rate, and/or otherwise pre-processing the signals.

The console 106 further includes a switch 118 configured to switch between the transmit circuit 114 and the receive circuit 116, e.g., by electrically connecting the transmit circuit 114 to the transducer array 110 for a transmit operation and electrically connecting the receive circuit 116 to the transducer array 110 for a receive operation. In an alternative instance, separate switches are employed such that the transmit circuit 114 has a switch and the receive circuit 116 has a different switch.

The console 106 further includes a transmit (TX) beamformer 120. The transmit beamformer 120 includes a pattern and transmission determiner 122. The pattern determines which elements are excited each transmission by the transmit circuit 114. Examples of suitable patterns include all of the elements (e.g., elements 0-95 for a 96 element array), even elements (e.g., 0, 2, 4, . . . ), odd elements (e.g., 1, 3, 5, . . . ), outer elements (e.g., elements 0-15 and 48-63 and not elements 16-47 for a 64 element array), inner elements (e.g., elements 16-47 and not elements 0-15 and 48-63 for a 64 element array), groups of elements (e.g., elements 0-3, 8-11, . . . ), etc.

The transmission determines how many transmissions are utilized to acquire data for each scanline. Examples of suitable transmissions include a single transmission, two transmissions, . . . , N transmissions for each scanline, where N is a positive integer. By way of example, in one instance a single transmission includes all of the elements, and, in another example, the single transmission is split into two transmissions, each with half of the elements, wherein the transmit energy level of each transmission is half of the single transmission, and an aggregate energy level of the two transmissions is equal to the energy level of the single transmission.

The console 106 further includes a receive (RX) beamformer 124 with scanline buffer memory 126. For receive operations, the RX beamformer 124 is configured to beamform, e.g., via delay-and-sum (e.g., a matched-filter beam-former, etc.) and/or other beamforming, the signals from the receive circuit 116 and construct a scanplane of scanlines of radiofrequency (RF) data or In-phase/Quadrature (IQ) data for the echoes for each receive operation. Where a trans-mission is split into multiple transmissions, the scanline for first transmission can be stored in the buffer memory 126 and combined with the scanline for second transmission to generate a scanline.

The console 106 further includes a scanline processor 128. The scanline processor 128 at least includes DTGC 130. The DTGC 130 is configured to digitally amplify the individual scanlines. As described in greater detail below, in one instance the DTGC 130, in an absence of water standoff enhancement artifact, applies gain factors to the scanlines based on the attenuation of tissue, and, in a presence of water standoff enhancement artifact, adaptively modulates the gain factor for each scanline in accordance with amount or degree of the water standoff enhancement artifact (e.g., only tissue, only water, or both tissue and water). The scanline processor 128 can be configured to further perform other processing.

The console 106 further includes image processor 132. The image processor 132 is configured to perform one or more of filtering (e.g., via a Finite Impulse Response (FIR) filter, an Infinite Impulse Response (IIR) filter, a band pass filter (BPF), etc.), in-phase and quadrature (I/Q) demodula-tion, envelope detection, dynamic range compression, com-pounding, dynamic range expansion, noise rejection, down-conversion, decimation. The image processor 132 outputs the processed scanlines as a frame data or a B-mode image.

The console 106 further includes other processing 134. In this example, the other processing 134 includes an adaptive gain. In one instance, the adaptive gain is configured to provide 2-D adaptive gain in both the axial and lateral directions to equalize the gain across the B-mode image, using known and/or other approaches. In another instance, the other processing 134 and/or the adaptive gain is omitted.

The console 106 further includes a scan converter 136. The scan converter 136 is configured to scan convert the frame to data or image into a coordinate system of a display monitor. The scan converter 136 can be configured to employ analog and/or digital scan converting techniques. The console 106 further includes a display 138. In this example, the scan converter 136 scan converts the frame to data or image into a coordinate system of the display monitor 138 and/or other display monitor.

The console 106 further includes a user interface (UI) 140. The UI 140 includes one or more input devices such as a button, a knob, a slider, a touchscreen, a mouse, a keyboard, etc. and/or other input device, and/or one or more output devices such as a visible, audible, etc. indicator. The UI 140 allows a user to control an operation of the system 102. For example, in one instance, the UI 140 receives an input indicative of a transmission scheme, e.g., a single transmission per scanline (original transmission mode) and/ or multiple scanlines per scan line (split transmission mode).

The console 106 further includes a controller 142. The controller 142 includes a processor(s) such as a micropro-cessor ($\mu$P), a central processing unit (CPU), a graphics processing unit (GPU), etc. The controller 142 is configured to control one or more of the transmit circuit 114, the receive circuit 116, the switch 118, the TX beamformer 120, the RX beamformer 124, the scanline processor 128, the image processor 132, the adaptive gain module 134, the scan converter 136, the display 138, and/or the user interface 140. One or more of these components of the console 106 can be implemented in software and/or hardware.

The console 106 further includes a computer readable medium 144 ("MEMORY"), which includes non-transitory medium and excludes transitory medium (signals, carrier waves, and the like). The computer readable medium 144 at least includes an adaptive image acquisition module 146. The adaptive image acquisition module 146 includes instructions that control at least the TX beamformer 120, the RX beamformer 124 and the scanline processor 128 based on an input, which includes one or more images from the image processor 132, one or more echo signals from the receive circuit 116, and/or one or more inputs via the U/I 140 from a user, to mitigate water standoff based enhancement artifact.

Briefly turning to FIGS. 2, 3, 4, 5, 6, 7 and 8, FIG. 2 illustrates an original single transmission for a scanline, and FIGS. 3, 4, 5, 6, 7 and 8 illustrate examples of split transmission for two transmissions per scanline from the original single transmission. FIGS. 3 and 4 illustrate an example where one transmission includes odd numbered elements and the other transmission includes even numbered elements. FIGS. 5 and 6 illustrate an example where one transmission includes outer elements and the other trans-mission includes inner elements. FIGS. 7 and 8 illustrate an example where one transmission includes a first set of groups of elements and the other transmission includes another sets of groups of the remaining elements. In FIGS. 2, 3, 4, 5, 6, 7 and 8, gray elements are excited elements and white elements are not excited.

Initially referring to FIG. 2, the transducer array 110 includes N elements, an element $202_1$, an element $202_2$, an element $202_3$, an element $202_4$, an element $202_5$, an element $202_6$, an element $202_7$, an element $202_8$, . . . , an element $202_{(N-7)}$, an element $202_{(N-6)}$, an element $202_{(N-5)}$, an element $202_{(N-4)}$, an element $202_{(N-3)}$, an element $202_{(N-2)}$, an element $202_{(N-1)}$, and an element $202_N$. In FIG. 2, all N of the elements, the element $202_1$, the element $202_2$, the element $202_3$, the element $202_4$, the element $202_5$, the element $202_6$, the element $202_7$, the element $202_8$, . . . , the element $202_{(N-7)}$, the element $202_{(N-6)}$, the element $202_{(N-5)}$, the element $202_{(N-4)}$, the element $202_{(N-3)}$, the element $202_{(N-2)}$, the element $202_{(N-1)}$, and the element $202_N$, are excited for each scanline.

In one instance, the split transmission for FIG. 2 is achieved through the voltage applied to the elements $202_1$, . . . $202_N$. For example, half energy transmissions could be achieved with the elements $202_1$, . . . $202_N$, i.e., in a system that includes hardware where transmit pressure can be controlled via a change of the applied voltage. The two transmissions in this case would be two replicate transmis-sions, each with half of the voltage applied, to the same elements $202_1$, . . . $202_N$. This results in two transmissions with half the energy, where together the two transmissions from the elements $202_1$, . . . $202_N$ in aggregate have the same energy as the original single transmission from the elements $202_1$, . . . $202_N$.

In FIG. 3, only odd numbered elements $202_1$, $202_3$, $202_5$, $202_7$, are excited, and, in FIG. 4, only even numbered elements $202_2$, $202_4$, $202_6$, $202_8$, are excited. Again, FIG. 3 represents one of two transmissions, and FIG. 4 represents the other of the two transmissions. In FIGS. 3 and 4, together, all N of the elements, the element $202_1$, the element $202_2$, the element $202_3$, the element $202_4$, the element $202_5$, the element $202_6$, the element $202_7$, the element $202_8$, . . . , the element $202_{(N-7)}$, the element $202_{(N-6)}$, the element $202_{(N-5)}$, the element $202_{(N-4)}$, the element $202_{(N-3)}$, the element $202_{(N-2)}$, the element $202_{(N-1)}$, and the element $202_N$, are excited for a scanline, but in two transmissions instead of one.

In FIG. 5, only outer elements $202_1$, $202_2$, $202_3$, $202_4$, ... $202_{(N-3)}$, $202_{(N-2)}$, $202_{(N-1)}$, and $202_N$, are excited, and, in FIG. 6, only inner elements $202_K$, ... $202_L$, are excited. Again, FIG. 5 represents one of two transmissions, and FIG. 6 represents the other of the two transmissions. In FIGS. 5 and 6, together, all N of the elements, the element $202_1$, the element $202_2$, the element $202_3$, the element $202_4$, ... the element $202_K$, ... the element $202_L$, ..., the element $202_{(N-3)}$, the element $202_{(N-2)}$, the element $202_{(N-1)}$, and the element $202_N$, are excited for a scanline, but in two transmissions instead of one.

In FIG. 7, a set of every other group of M elements $202_{1-M}$, ... are excited, and, in FIG. 8, an opposite set of every other group of M elements $202_{(M+1)-2M}$, ... are excited. Again, FIG. 7 represents one of two transmissions, and FIG. 8 represents the other of the two transmissions. In FIGS. 7 and 8, together, all N of the elements, the element $202_K$, ..., $202_L$, the element $202_3$, the element $202_4$, the element $202_5$, the element $202_6$, the element $202_7$, the element $202_8$, ..., the element $202_{(N-7)}$, the element $202_{(N-6)}$, the element $202_{(N-5)}$, the element $202_{(N-4)}$, the element $202_{(N-3)}$, the element $202_{(N-2)}$, the element $202_{(N-1)}$, and the element $202_N$, are excited for a scanline, but in two transmissions instead of one.

Again, FIGS. 3, 4, 5, 6, 7 and 8 illustrate examples of split transmits for two transmits per each scanline. In general, all permutations of splitting a single transmission across multiple transmissions are contemplated herein. In addition, it is to be appreciated that the single transmission described in connection with FIG. 2 may not include exciting all of the elements of the transducer. Regardless, the split transmission will each have less energy than the original transmission from less than all of the elements.

Moving to FIGS. 9 and 10, FIG. 9 schematically illustrates an example of the adaptive image acquisition module 144. In this example, the adaptive image acquisition module 144 includes an image analyzer 902. With reference to FIGS. 9 and 10, the controller 142 receives, as input, the 2-D frame or image generated by the image processor 132, and outputs a signal indicating a presence of a water standoff in response to determining there is a water standoff from the 2-D frame or image. The controller 142 does not output the signal in response to determining that there is no water standoff and/or outputs a signal indicating there is no water standoff.

The image analyzer 902 is configured to process the 2-D frame or image to determine whether there is a water standoff. In general, a water standoff region in the 2-D frame or image, relative to regions of tissue in the 2-D frame or image, will manifest as flat pixels with granular noise (e.g., speckle) in the 2-D frame or image. In one instance, the image analyzer 902 is configured to process the 2-D frame or image to remove and/or reduce such noise. Example approaches to remove and/or reduce noise include spatial filtering, anisotropic diffusion, artificial intelligence (AI) and/or other approach, e.g., that enhances the image by reducing noise while preserving structure.

With or without removing and/or reducing the noise, the image analyzer 902 is configured to identify any water standoff and segment the water standoff. In one instance, the image analyzer 902 is configured to employ an edge detection algorithm to identify a boundary of a water standoff for segmentation. Examples of edge detection algorithms include operators which use convolution kernels to approximate a gradient of the image intensity function, smoothing and then detecting a gradient, etc. Other algorithms such as AI based algorithms are also contemplated herein.

Where the image analyzer 902 does not find a water standoff, the image analyzer 902 continues to analyze the 2-D frames or images generated by the image processor 132 as they are received. Where the image analyzer 902 finds a water standoff, the image analyzer 902 transmits a signal indicating there is a water standoff to the TX beamformer 120, the RX beamformer 124 and the scanline processor 128. As discussed herein, relative to tissue, water has little attenuation to ultrasound pressure waves, and the echo at the water-tissue interface is large relative to tissue echoes, which can result in saturation or clipping of the digital signal output by the receive circuit 116 (FIG. 1).

The pattern and transmission determiner 122, in response to the signal indicating a water standoff is detected, adjusts the transmit operation to mitigate saturation. For example, in one instance where all of the elements 112 of the transducer array 110 are excited in a single transmit (original transmit mode) for each scanline, the signals invoke the pattern and transmission determiner 122 to switch modes from original transmit mode (all of the elements 112 in a single transmit) to a split transmit mode in which excitation is split such that there are multiple transmits per scanline where less than all of the elements are excited for each transmit.

With two transmits for each scanline, each transmit will have less energy than the original single transmit, reducing the energy of each transmit and mitigating saturation, and both transmits together in aggregate will have the same overall energy as the original single transmit, so that the same overall energy is maintained and image quality is not compromised. The energy of each of the two transmits for each scanline can be equal (e.g., half of the energy of the original single transmit) or otherwise, as long as the aggregate of all the transmits has the same overall energy as the original single transmit.

Continuing with the example of two transmissions for a split transmission, the receive circuit 116 receives the echo signal corresponding the first transmission of a split acquisition and processes the echo signal as described herein, e.g., amplifies, digitizes, etc. the echo signal, and RX beamformer 124 stores the digitized signal in the buffer memory 126. The receive circuit 116 receives the echo signal corresponding to the second transmission of the split acquisitions and processes the echo signal as described herein. The RX beamformer 124 then combines the two signals and beamforms (e.g., as described herein) the combined signal to generate a single scanline or a plurality of scanlines according to the configuration of the beamformer.

The scanline processor 128 receives the scanlines generated for all of split transmission, and the DTGC 130 applies a gain along each scanline (i.e., in the axial/depth direction) based on whether a scanline corresponds to a path through only tissue, a path through only the water standoff, or a path through tissue and water standoff. For a scanline with a path through tissue, the original DTGC is applied to provide a uniform image. For example, the transmit signal generally increases in strength up to the focal point and then decays. In this instance, the DTGC 130 applies a gain to equalize the signal strength. For example, the DTGC 130 increases the gain before the focal point. For a scanline with a path through only water standoff, there is no tissue before the focal point to attenuate the signal, and the DTGC 130 decreases the gain before the focal point. For a scanline with a path through tissue and water standoff, the DTGC 130 applies a gain according to the degree the path is through the tissue and the water standoff.

Moving to FIGS. 11 and 12, FIG. 11 schematically illustrates another example of the adaptive image acquisition module 144. In this example, the adaptive image acquisition module 144 includes an echo signal analyzer 1102. With reference to FIGS. 11 and 12, the controller 142 receives, as input, the echo signal output by the receive circuit 116, and outputs a signal indicating whether there is a presence of a water standoff. For this, the echo signal analyzer 1102 is configured to process the echo signal to determine whether the echo signal is saturated, where saturation indicates a presence of a water standoff.

Figure 13:
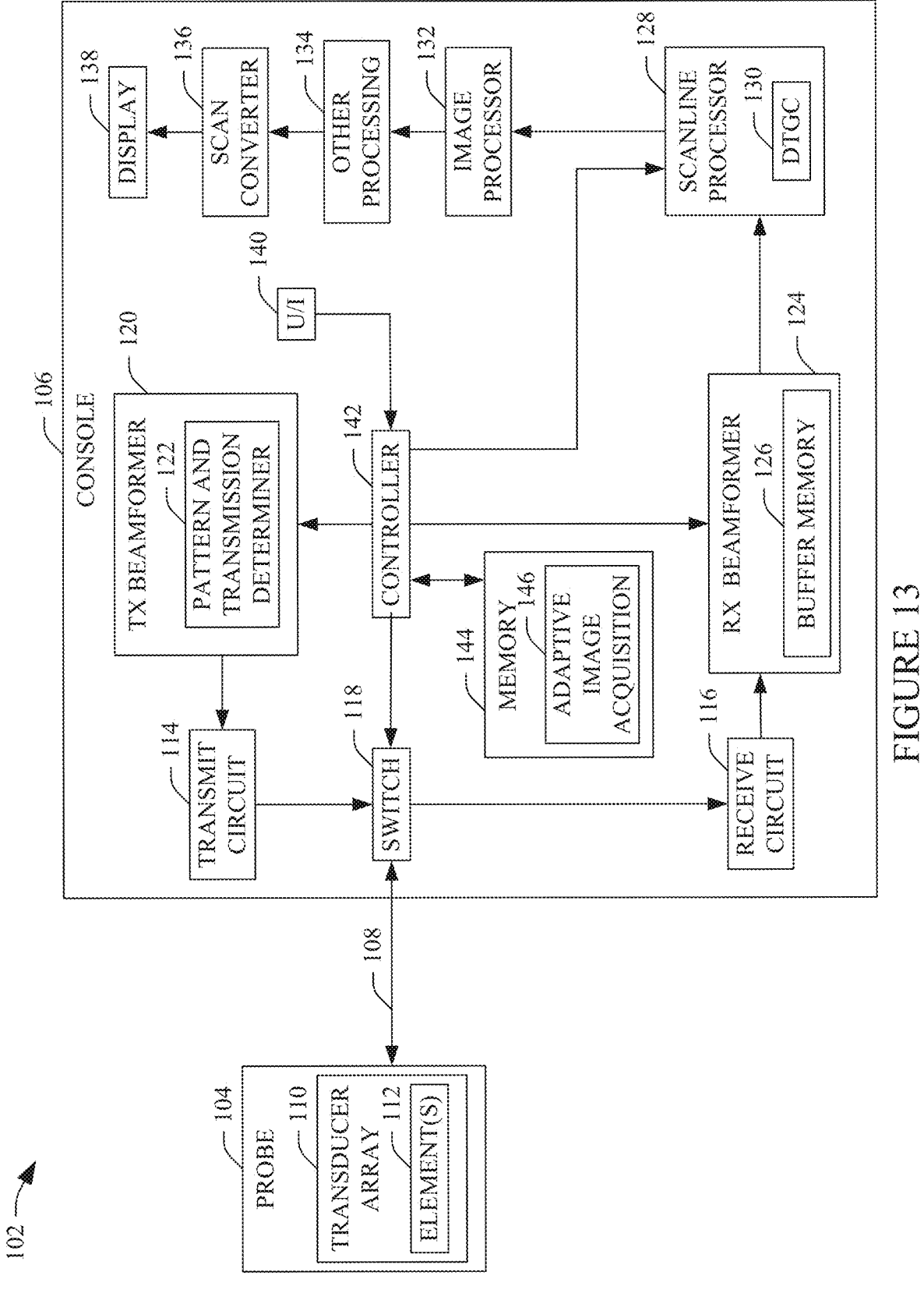
FIG. 13 schematically illustrates the ultrasound imaging configured to switch to split transmission mode on-demand based on a user input in accordance with an aspect of an embodiment(s) herein.

Moving to FIG. 13, in this example, the imaging system 102 can be controlled to switch from the original transmission mode to split transmission mode on-demand based on a user input, e.g., via the user interface (U/I) 140 and/or otherwise. In one instance, the user observing the displayed image may invoke split transmission mode via the user interface 140 upon identifying the water standoff enhancement artifact in the displayed image. In another instance, the user anticipating water standoff enhancement artifact may invoke split transmission mode via the user interface 140 before identifying the water standoff enhancement artifact in the displayed image. In another instance, the user can toggle between original transmission and split transmission modes on-demand based on a user input and/or automatically.

In another instance, a variation includes a combination of two or more of the embodiments of FIGS. 10, 12 and/or 13, and/or other approach. In any instance, the image analyzer 902, the echo signal analyzer 1102 and/or the user can switch to split transmission mode. Additionally, or alternatively, the image analyzer 902, the echo signal analyzer 1102 and/or the user can switch from split transmission mode to full transmission mode.

Figure 14:
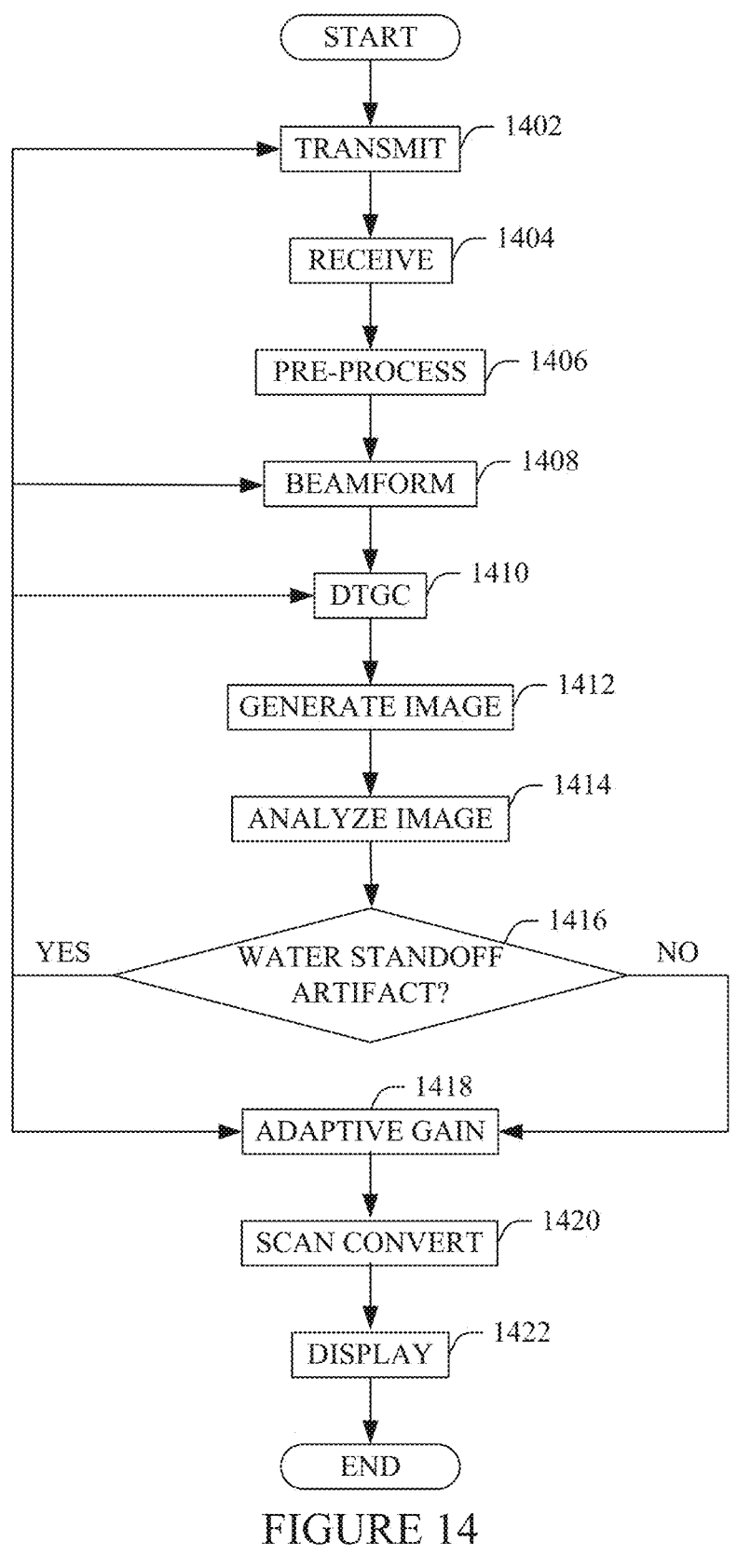
FIG. 14 illustrates a non-limiting example of a flow chart for a computer-implemented method for mitigating water standoff enhancement artifact based on image analysis, in accordance with an embodiment(s) herein.

FIG. 14 illustrates a non-limiting example of a flow chart for a computer-implemented method for mitigating water standoff enhancement artifact based on image analysis. It is to be appreciated that the ordering of the acts in the method is not limiting. As such, other orderings are contemplated herein. In addition, one or more acts may be omitted, and/or one or more additional acts may be included.

At 1402, an ultrasound pressure wave is transmitted in accordance with a selected protocol, as disclosed herein and/or otherwise. Initially, the protocol corresponds to a protocol for scanning before, during and/or after a procedure which does not include a water standoff to fill a cavity resulting from an excision of tissue of interest such as a tumor. In this example, the protocol results in a single transmission for each scanline. At 1404, an echo created in response to the single transmission is received, as disclosed herein and/or otherwise. At 1406, the echo is pre-processed, as disclosed herein and/or otherwise.

At 1408, the pre-processed echo signal is beamformed to generate a scanline, as disclosed herein and/or otherwise. This includes beamforming the pre-processed echo signal created in response to the single transmission. At 1410, DTGC is applied to each beamformed scanline, as disclosed herein and/or otherwise. Again, the transmit signal generally increases in strength up to the focal point and then decays, and the DTGC 130 is applied to equalize the signal strength. At 1412, the scanlines are processed to generate a 2-D frame or image, as disclosed herein and/or otherwise.

At 1414, the image is analyzed for a presence of a water standoff, as disclosed herein and/or otherwise. At 1416, it is determined whether a water standoff is present, as disclosed herein and/or otherwise. Where a water standoff is not detected, at 1418, an adaptive gain is applied in 2-D across the image for uniformity, as disclosed herein and/or otherwise. At 1420, the image is scan converted, as disclosed herein and/or otherwise. At 1422, the image is displayed, as disclosed herein and/or otherwise.

Where a water standoff is detected, the TX beamformer 120, the RX beamformer 124 and the scanline processor 128 are switched from original transmission mode to split transmission mode in which each transmission is split into multiple transmissions (each with an energy less than the energy of the original transmission signal) via the TX beamformer 120, the RX beamformer 124 combines the echo signals for each of the multiple transmissions, and the scanline processor 128 applies DTGC based on whether a scanline corresponds to a transmission through tissue or the water standoff, as disclosed herein and/or otherwise.

In addition, the current image is processed at 1418 where an adaptive gain is applied in 2-D across the image for uniformity, as disclosed herein and/or otherwise, scan converted at 1420, as disclosed herein and/or otherwise, and then displayed, as disclosed herein and/or otherwise. In one instance, splitting the transmission energy across multiple transmissions for each scanline mitigates echo signal saturation, combining the echo signal ensures the original energy maintained, and applying the DTGC individually allows for compensating the scanlines traversing the water standoff, reducing water standoff enhancement artifact.

Figure 15:
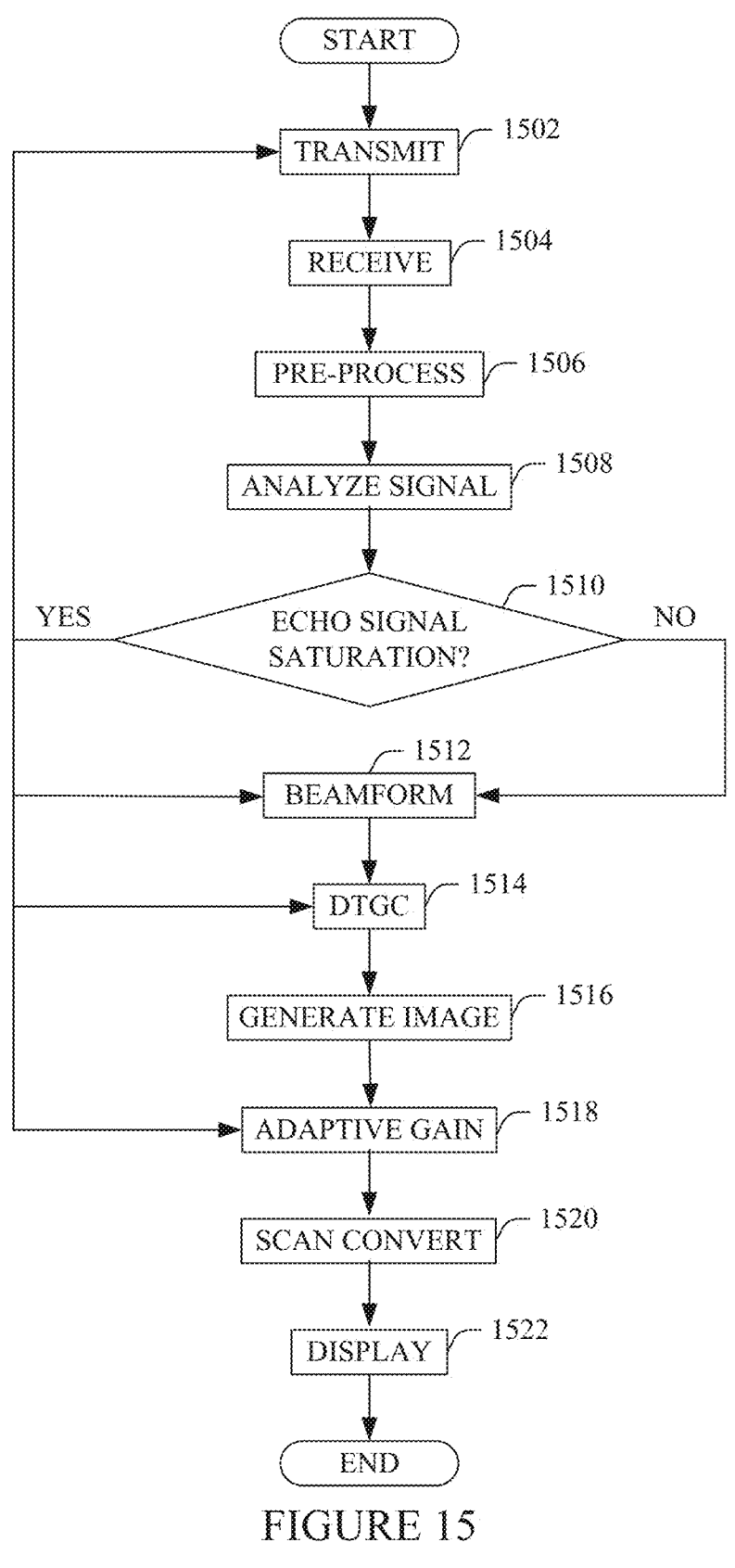
FIG. 15 illustrates a non-limiting example of a flow chart for a computer-implemented method for mitigating water standoff enhancement artifact based on echo signal analysis, in accordance with an embodiment(s) herein.

FIG. 15 illustrates a non-limiting example of a flow chart for a computer-implemented method for mitigating water standoff enhancement artifact based on echo signal analysis. It is to be appreciated that the ordering of the acts in the method is not limiting. As such, other orderings are contemplated herein. In addition, one or more acts may be omitted, and/or one or more additional acts may be included.

At 1502, an ultrasound pressure wave is transmitted in accordance with a selected protocol, as disclosed herein and/or otherwise. Initially, the protocol corresponds to a protocol for scanning before, during and/or after a procedure which does not include a water standoff to fill a cavity resulting from an excision of tissue of interest such as a tumor. In this example, the protocol results in a single transmission for each scanline. At 1504, an echo created in response to the single transmission is received, as disclosed herein and/or otherwise. At 1506, the echo is pre-processed, as disclosed herein and/or otherwise.

At 1508, the echo signal is analyzed for saturation, as disclosed herein and/or otherwise. At 1510, it is determined whether the echo signal is saturated, as disclosed herein and/or otherwise. Where saturation is not detected, at 1512, the pre-processed echo signal is beamformed to generate a scanline, as disclosed herein and/or otherwise. Again, this includes beamforming the pre-processed echo single created in response to the single transmission. At 1514, DTGC is applied to each beamformed scanline, as disclosed herein and/or otherwise. Again, the transmit signal generally increases in strength up to the focal point and then decays, and the DTGC 130 is applied to equalize the signal strength.

At 1516, the scanlines are processed to generate a 2-D frame or image, as disclosed herein and/or otherwise. At 1518, an adaptive gain is applied in 2-D across the image for uniformity, as disclosed herein and/or otherwise. At 1520, the image is scan converted, as disclosed herein and/or otherwise. At 1522, the image is displayed, as disclosed herein and/or otherwise.

Where saturation is detected at 1510, the TX beamformer 120, the RX beamformer 124 and the scanline processor 128 are switched, for the next transmission, from original transmission mode to split transmission mode in which each transmission is split into multiple transmissions (each with an energy less than the energy of the original transmission signal) via the TX beamformer 120, the RX beamformer 124 combines the echo signals for each of the multiple transmissions, and the scanline processor 128 applies DTGC based on whether a scanline corresponds to a transmission through tissue or the water standoff, as disclosed herein and/or otherwise.

In addition, at 1512, the pre-processed echo signal is beamformed to generate a scanline, as disclosed herein and/or otherwise. At 1514, DTGC is applied to each beamformed scanline, as disclosed herein and/or otherwise. At 1516, the scanlines are processed to generate a 2-D frame or image, as disclosed herein and/or otherwise. At 1518, an adaptive gain is applied in 2-D across the image for uniformity, as disclosed herein and/or otherwise. At 1520, the image is scan converted, as disclosed herein and/or otherwise. At 1522, the image is displayed, as disclosed herein and/or otherwise.

Again, in one instance, splitting the transmission energy across multiple transmissions for each scanline mitigates echo signal saturation, combining the echo signal ensures the original energy maintained, and applying the DTGC individually allows for compensating the scanlines traversing the water standoff, reducing water standoff enhancement artifact.

Figure 16:
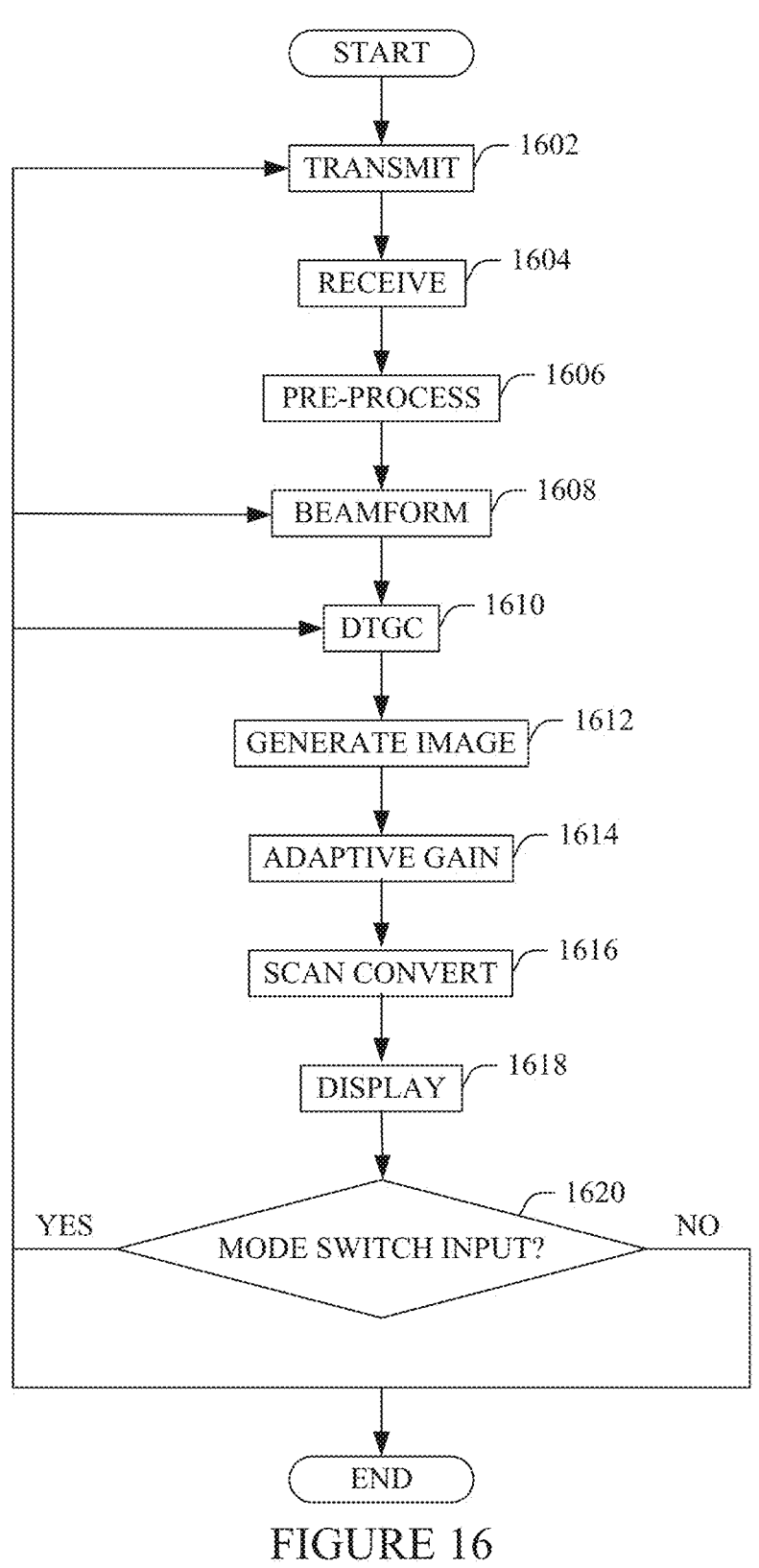
FIG. 16 illustrates a non-limiting example of a flow chart for a computer-implemented method for mitigating water standoff enhancement artifact based on user input analysis, in accordance with an embodiment(s) herein.
Figure 17:
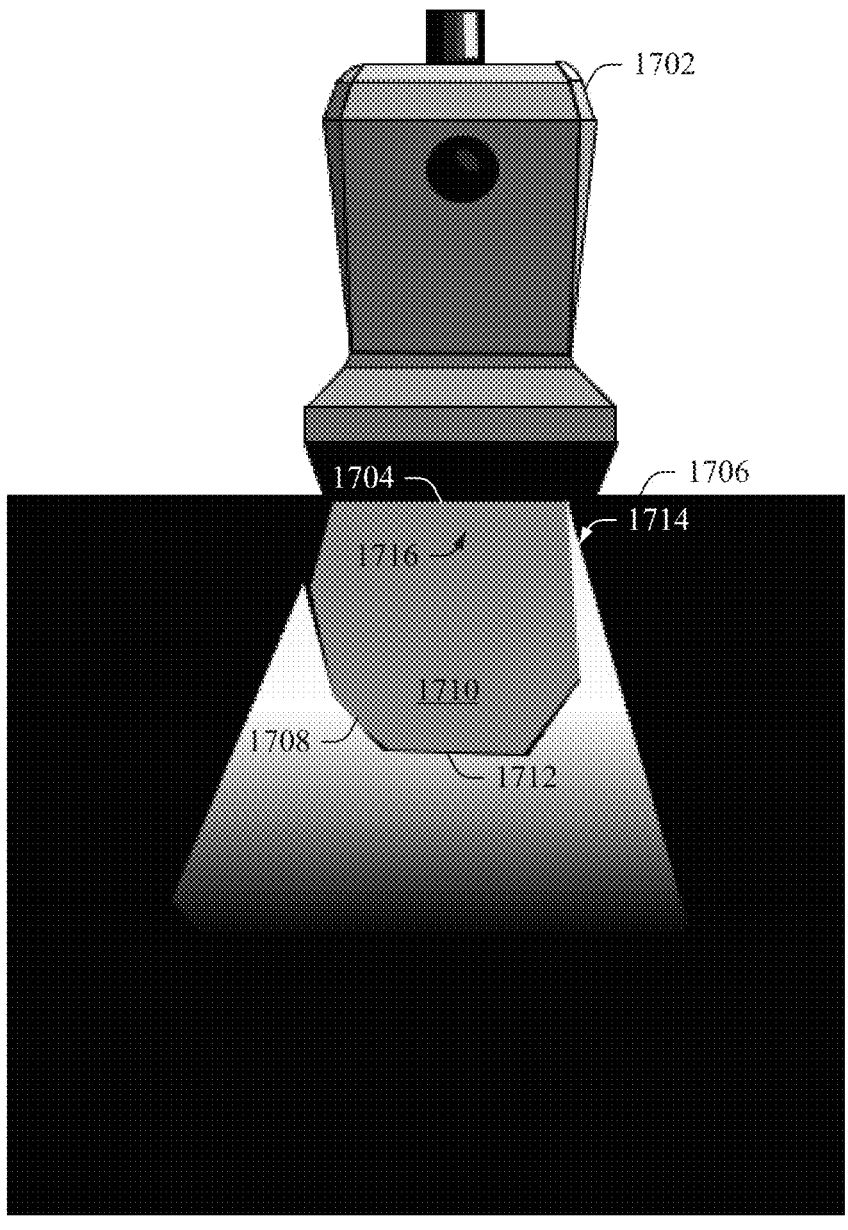
FIG. 17 shows an example of a water standoff in connection with excised tissue.

FIG. 16 illustrates a non-limiting example of a flow chart for a computer-implemented method for mitigating water standoff enhancement artifact based on user input. It is to be appreciated that the ordering of the acts in the method is not limiting. As such, other orderings are contemplated herein. In addition, one or more acts may be omitted, and/or one or more additional acts may be included.

At 1602, an ultrasound pressure wave is transmitted in accordance with a selected protocol, as disclosed herein and/or otherwise. Initially, the protocol corresponds to a protocol for scanning before, during and/or after a procedure which does not include a water standoff to fill a cavity resulting from an excision of tissue of interest such as a tumor. In this example, the protocol results in a single transmission for each scanline. At 1604, an echo created in response to the single transmission is received, as disclosed herein and/or otherwise. At 1606, the echo is pre-processed, as disclosed herein and/or otherwise.

At 1608, the pre-processed echo signal is beamformed to generate a scanline, as disclosed herein and/or otherwise. This includes beamforming the pre-processed echo signal created in response to the single transmission is received. At 1610, DTGC is applied to each beamformed scanline, as disclosed herein and/or otherwise. Again, the transmit signal generally increases in strength up to the focal point and then decays, and the DTGC 130 is applied to equalize the signal strength. At 1612, the scanlines are processed to generate a 2-D frame or image, as disclosed herein and/or otherwise.

At 1614, an adaptive gain is applied in 2-D across the image for uniformity, as disclosed herein and/or otherwise. At 1616, the image is scan converted, as disclosed herein and/or otherwise. At 1618, the image is displayed, as disclosed herein and/or otherwise. At 1620, it is determined whether a user input switched from original transmission mode to split transmission mode. Where the user did not switch from original transmission mode to split transmission mode, acts 1602 through 1620 are repeated.

Where the user switched modes, the TX beamformer 120, the RX beamformer 124 and the scanline processor 128 are switched from original transmission mode to split transmission mode in which each transmission is split into multiple transmissions (each with an energy less than the energy of the original transmission signal) via the TX beamformer 120, the RX beamformer 124 combines the echo signals for each of the multiple transmissions, and the scanline processor 128 applies DTGC based on whether a scanline corresponds to a transmission through tissue or the water standoff, as disclosed herein and/or otherwise.

Again, in one instance, splitting the transmission energy across multiple transmissions for each scanline mitigates echo signal saturation, combining the echo signal ensures the original energy maintained, and applying the DTGC individually allows for compensating the scanlines traversing the water standoff, reducing water standoff enhancement artifact.

The above can be implemented by way of computer readable instructions, encoded, or embedded on the computer readable storage medium, which, when executed by a computer processor, cause the processor to carry out the described acts or functions. Additionally, or alternatively, at least one of the computer readable instructions is carried out by a signal, carrier wave or other transitory medium, which is not computer readable storage medium.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include such additional elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only and are thus not intended to limit in any way the definition and/or meaning of the term "computer". The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present disclosure. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used as practice in some jurisdictions require them, but this should not be taken to mean that the features in the dependent claims are mutually exclusive.

What is claimed is:

1. An ultrasound imaging system, comprising:
a transducer array configured to transmit, alternatively, a single transmission for a scanline with a set of transducer elements in a first transmission mode and a split transmission for the scanline with the set of transducer elements in a split transmission mode,
wherein the split transmission includes at least a first transmission with a first subset of the set of transducer elements and a second transmission with a second subset of the set of transducer elements, and
wherein the set of transducer elements for the single transmission is split into the first subset of the set of transducer elements and the second subset of the set of transducer elements for the split transmission;
a beamformer configured to beamform an echo signal corresponding to the single transmission in the first transmission mode and a combination of echo signals corresponding to the first transmission and the second transmission in the split transmission mode;
a controller configured to detect a presence of water standoff enhancement artifact based on the echo signal in the first transmission mode and switch the transducer array, the beamformer and a scanline processor from the first transmission mode to the split transmission mode for a subsequent transmission in response to detecting the presence of the water standoff enhancement artifact;
the scanline processor configured to adaptively apply digital time gain compensation to the scanline, wherein a first gain is applied to the scanline corresponding to a transmission traversing tissue in the first transmission mode and a second gain is applied to the scanline corresponding to a transmission traversing a water standoff-tissue boundary, to correct for the water standoff enhancement artifact, wherein the transmission traversing the water standoff-tissue boundary causes the water standoff enhancement artifact in the split transmission mode;
an image processor configured to generate an image based on the scanline, and
a display configured to display the image.

2. The ultrasound imaging system of claim 1, wherein each of the first transmission and the second transmissions has a transmit energy less than a transmit energy of the single transmission for the scanline.

3. The ultrasound imaging system of claim 2, wherein an aggregate of the transmit energy of each of the first transmission and second transmissions equals the transmit energy of the single transmission for the scanline.

4. The ultrasound imaging system of claim 1, wherein the controller is configured to detect the water standoff enhancement artifact based on an analysis of the image.

5. The ultrasound imaging system of claim 4, wherein the analysis of the image includes edge detection to detect a boundary of the water standoff in the image.

6. The ultrasound imaging system of claim 1, wherein the controller is configured to detect the water standoff enhancement artifact based on an analysis of the echo signal.

7. The ultrasound imaging system of claim 6, wherein the analysis of the echo signal identifies signal saturation.

8. The ultrasound imaging system of claim 1, wherein the controller is configured to switch from the first transmission mode to the split transmission mode based on a user input.

9. The ultrasound imaging system of claim 1, wherein one of:

the first transmission includes only even numbered elements and the second transmission includes only odd numbered elements.

10. The ultrasound imaging system of claim 1, wherein an energy level of each of the first transmission and the second transmission has half of an energy level of the single transmission.

11. A computer-implemented method, comprising:

transmitting, alternatively, a single transmission for a scanline with a set of transducer elements in a first transmission mode and a split transmission for the scanline with the set of transducer elements in a split transmission mode, wherein the split transmission includes at least a first transmission with a first subset of the set of transducer elements and a second transmission with a second subset of the set of transducer elements, and wherein the set of transducer elements for the single transmission is split into the first subset of the set of transducer elements and the second subset of the set of transducer elements for the split transmission;

beamforming an echo signal corresponding to the single transmission in the first transmission mode and a combination of echo signals corresponding to the first transmission and the second transmission in the split transmission mode;

detecting a presence of water standoff enhancement artifact based on the echo signal in the first transmission mode;

switching the transducer array, the beamformer and the scanline processor from the first transmission mode to the split transmission mode for a subsequent transmission in response to detecting the presence of the water standoff enhancement artifact;

adaptively applying digital time gain compensation to the scanline, wherein a first gain is applied to the scanline corresponding to a transmission traversing tissue in the first transmission mode and a second gain is applied to the scanline corresponding to a transmission traversing a water standoff-tissue boundary, to correct for the water standoff enhancement artifact, wherein the transmission traversing the water standoff-tissue boundary causes the water standoff enhancement artifact, in the split transmission mode;

generating an image based on the scanline, and displaying the image.

12. The computer-implemented method of claim 11, wherein each of the first transmission and the second transmission has a transmit energy less than a transmit energy of the single transmission for the scanline.

13. The computer-implemented method of claim 11, further comprising:

analyzing the image to detect the water standoff enhancement artifact.

14. The computer-implemented method of claim 11, further comprising:

analyzing the echo signal to detect the water standoff enhancement artifact by detecting signal saturation.

15. The computer-implemented method of claim 11, further comprising:

switching from the first transmission mode to the split transmission mode based on a user input.

16. A non-transitory computer readable medium encoded with computer executable instructions, which, when executed by a processor, cause the processor to:

transmit, alternatively, a single transmission for a scanline with a set of transducer elements in a first transmission mode and a split transmission for the scanline with the set of transducer elements in a split transmission mode, wherein the split transmission includes at least a first transmission with a first subset of the set of transducer elements and a second transmission with a second subset of the set of transducer elements, and wherein the set of transducer elements for the single transmission is split into the first subset of the set of transducer elements and the second subset of the set of transducer elements for the split transmission;

beamform an echo signal corresponding to the single transmission in the first transmission mode and a combination of echo signals corresponding to the first transmission and the second transmission in the split transmission mode;

detect a presence of water standoff enhancement artifact based on the echo signal in the first transmission mode;

switch the transducer array, the beamformer and the scanline processor from the first transmission mode to the split transmission mode for a subsequent transmission in response to detecting the presence of the water standoff enhancement artifact;

adaptively apply digital time gain compensation to the scanline, wherein a first gain is applied to the scanline corresponding to a transmission traversing tissue in the first transmission mode and a second gain is applied to the scanline corresponding to a transmission traversing a water standoff-tissue boundary, to correct for the water standoff enhancement artifact, wherein the transmission traversing the water standoff-tissue boundary causes the water standoff enhancement artifact, in the split transmission mode;

generate an image based on the scanline, and display the image.

17. The non-transitory computer readable medium of claim 16, wherein each of the first transmission and the second transmission has a transmit energy less than a transmit energy of the single transmission for the scanline.

18. The non-transitory computer readable medium of claim 17, wherein the instructions further cause the processor to:

analyze the image to detect the water standoff enhancement artifact.

19. The non-transitory computer readable medium of claim 17, wherein the instructions further cause the processor to:

analyze the echo signal to detect the water standoff enhancement artifact by detecting signal saturation.

20. The non-transitory computer readable medium of claim 16, wherein the instructions further cause the processor to:

switch from the first transmission mode to the split transmission mode based on a user input.

* * * * *